US00PP12464P2

(12) United States Plant Patent
Zary

(10) Patent No.: US PP12,464 P2
(45) Date of Patent: Mar. 19, 2002

(54) HYBRID TEA ROSE PLANT NAMED 'JACWOTTE'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/400,725

(22) Filed: Sep. 21, 1999

(51) Int. Cl.[7] ..... A01H 5/00
(52) U.S. Cl. ..... Plt./130
(58) Field of Search ..... Plt./130, 135, 137

*Primary Examiner*—Howard J. Locker
(74) *Attorney, Agent, or Firm*—Klarquist Sparkman Campbell Leigh & Whinston, LLP

(57) ABSTRACT

A hybrid tea rose plant having large, high centered, blushed pink flowers; long cutting stems; dark green, glossy foliage; good disease resistance; and vigorous, upright growth.

1 Drawing Sheet

The present invention relates to a new and distinct variety of rose plant of the hybrid tea class which was originated by me by crossing the variety 'JACyap' (not patented), with an unnamed seedling (not patented).

The primary objective of this breeding was to produce a new rose variety having the high centered flower form and long cutting stems of the female parent, combined with the dark, glossy foliage, good disease resistance and vigorous, upright growth of the male parent. The objective was substantially achieved, along with other desirable improvements, as evidenced by the following unique combination of characteristics that are outstanding in the new variety and that distinguish it from its parents, as well as from all other varieties of which I am aware:

1. Soft cream, blushed pink flower color;
2. Large, high centered flowers;
3. Vigorous, upright growth;
4. Dark green, semi-glossy leaves;
5. Good disease resistance; and
6. Long cutting stems.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACyap' (unnamed seedling×unnamed seedling — not patented).

*Pollen parent.*—Unnamed seedling (JAColite — U.S. Plant Pat. No. 4,167×Silver Jubilee — not patented).

Classification:

*Botanical.*—*Rosa hybrida.*

*Commercial.*—Hybrid tea.

FLOWER

Observations made from specimens grown in a garden environment at Somis, Calif. from March 1999 to August 1999.

Blooming habit: Continuous.

Bud:

*Size.*—1¾ inches long when the petals start to unfurl.

*Form.*—The bud form is long; pointed ovoid.

*Color.*—When sepals first divide, bud color is Yellow-Group 2C blushed with Red Group 46D where exposed to bright direct sunlight. When half blown, the upper sides of the petals are Yellow-Orange Group 17D on the bottom ¼ of the upper surface, and Orange Group 27D on the rest of the surface, except for Red Group 49D on the petal edge; and the lower sides of the petals are Yellow-Orange Group 17D in the bottom ¼ of the petal and Orange Group 27D on the rest of the surface, except for Red Group 49D on the petal edge.

*Sepals.*—Color: Green Group 138B except where exposed to bright sunlight, then it is blushed with Greyed-Purple Group 183D. Surface texture: Covered in fine hairs. There are three normally appendaged sepals. There are two unappendaged sepals with hairy edges.

*Receptacle.*—Color: Green Group 137A. Shape: Funnel. Size: Medium, about ¼ inch×⅜ inch. Surface: Smooth.

*Peduncle.*—Length: Medium, about 2¼ to 2½ inches. Surface: Rough; glandular. Color: Green Group 137A, but often Greyed-Purple Group 183A when exposed to bright sun. Strength: Stiff; erect.

Bloom:

*Size.*—Large. Average open size is 4½ inches.

*Borne.*—Singly.

*Stems.*—Strength: Strong. Average length is about 14–18 inches.

*Form.*—When first open, bloom is high centered. Permanence: Retains its form to the end; outer petals curl back with some quilling.

*Petalage.*—Number of petals under normal conditions: 35.

*Color.*—The upper sides of the petals are Yellow-Orange Group 17D on the bottom ¼ of the petal, and then Orange Group 27D on the rest of the petal surface, except for Red Group 49D on the petal edge. The reverse sides of the petals are Yellow-Orange Group 17D on the bottom ¼ of the petal, and then Orange Group 27D on the rest of the surface, except for Red Group 49D on the petal edge. The base of each petal has a small, ¼ inch×¼ inch Yellow-Orange Group 21B half moon at the point of attachment on both petal surfaces. The major color on the upper side is Orange Group 27D.

*Variegations.*—None.

*Discoloration.*—The general tonality at the end of the first day: No change. At the end of the third day: No change. There is no change until petal drop.

*Fragrance.*—Moderate; anise.

Petals:

*Texture.*—Thick.

*Shape.*—Round.

*Form.*—Tips slightly recurved; edges slightly quilled.

*Arrangement.*—Imbricated. There are no petaloids in the center.

*Persistence.*—Petals drop off cleanly before drying.

*Lastingness.*—On the plant: Long (about five to six days). As a cut flower: Long (about eight to nine days).

Reproductive parts:

*Anthers.*—Size: Medium. Quantity: many. Color: Yellow-Orange Group 21C. Arrangement: Regular around the styles.

*Filaments.*—Color: Red Group 42A.

*Pollen.*—Present.

*Styles.*—Color: Red Group 53A.

*Stigmas.*—Color: Orange-White Group 159C.

Plant:

*Form.*—Bush.

*Growth.*—Vigorous; upright; branching. At maturity, height is 5 feet and width is 3½ feet.

Foliage: Number of leaflets on normal mid-stem leaves: Five.

*Size.*—Large (6 to 6½ inches long×4½ to 5 inches wide).

*Quantity.*—Abundant.

*Color.*—New foliage: Upper and lower surfaces: Greyed-Purple Group 187A. Old foliage: Upper surface: Green Group 139A. Lower surface: Green Group 139B.

Leaflets:

*Shape.*—Pointed oval.

*Texture.*—Leathery; glossy.

*Edge.*—Serrated.

*Serration.*—Single; small.

*Petiole rachis.*—Color: Upper surface: Green Group 137B with some Greyed-Purple Group 187A along the rachis. Lower surface: Green Group 137B.

*Petiole underside.*—Rough, with prickles.

*Stipules.*—Long (about ¾ to 1 inch long); thin; serrated, bearded.

*Disease resistance.*—Resistant to mildew and rust; susceptible to blackspot under normal growing conditions.

Wood:

*New wood.*—Color: Greyed-Purple Group 187A. Bark: Smooth.

*Old wood.*—Color: Green Group 139A. Bark: Smooth.

Prickles:

*Quantity.*—On the main canes from base: Ordinary. On laterals from main canes: Ordinary.

*Form.*—Medium; hooked downward.

*Color when young.*—Greyed-Purple Group 187A.

*Color when mature.*—Greyed-Orange Group 177A.

Small prickles:

*Quantity.*—On main stalks: None. On laterals: None.

I claim:

1. A new and distinct variety of rose plant of the hybrid tea class, substantially as herein shown and described, characterized particularly by its large, high centered, blushed pink flowers; long cutting stems; dark green, glossy foliage; good disease resistance; and vigorous, upright growth.

* * * * *

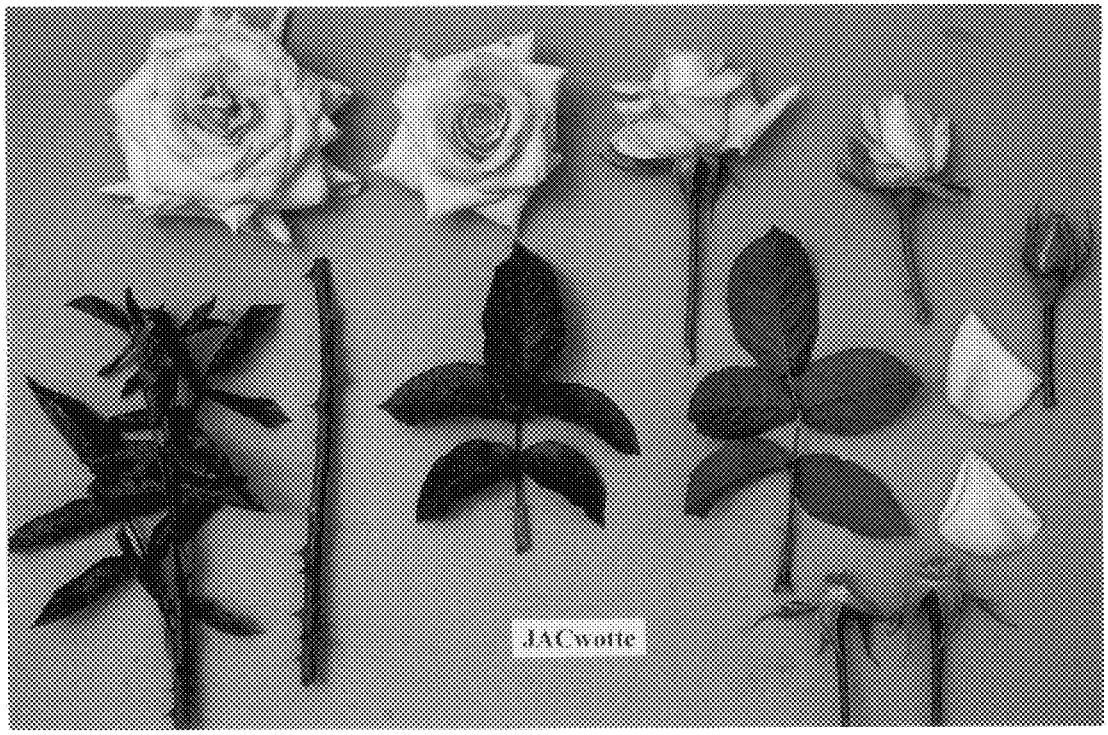
JACwotte